United States Patent [19]

Berg et al.

[11] Patent Number: 5,152,876

[45] Date of Patent: * Oct. 6, 1992

[54] SEPARATION OF METHYLENE CHLORIDE FROM THE LOWER ALCOHOLS BY EXTRACTIVE DISTILLATION

[75] Inventors: Lloyd Berg, 1314 S. Third Ave., Bozeman, Mont. 59715; Zuyin Yang, Bozeman, Mont.

[73] Assignee: Lloyd Berg, Bozeman, Mont.

[ * ] Notice: The portion of the term of this patent subsequent to Jul. 21, 2009 has been disclaimed.

[21] Appl. No.: 675,817

[22] Filed: Mar. 27, 1991

[51] Int. Cl.$^5$ .................. B01D 3/40; C07C 17/38; C07C 29/84
[52] U.S. Cl. ............................... 203/57; 203/58; 203/59; 203/60; 203/61; 203/62; 203/63; 203/64; 568/913; 568/918; 570/262
[58] Field of Search ............... 203/60, 59, 61, 64, 203/58, 63, 62, 57; 568/913, 918; 570/262

[56] References Cited

U.S. PATENT DOCUMENTS

| | | | |
|---|---|---|---|
| 1,566,819 | 12/1925 | Carter | 568/594 |
| 2,856,331 | 10/1958 | Rosenthal et al. | 203/18 |
| 2,865,955 | 12/1958 | Ascherl et al. | 560/248 |
| 5,051,153 | 9/1991 | Berg | 570/262 |

FOREIGN PATENT DOCUMENTS

| | | | |
|---|---|---|---|
| 142183 | 6/1980 | German Democratic Rep. | 203/64 |
| 59-76026 | 4/1984 | Japan | 570/262 |
| 61-93147 | 5/1986 | Japan | 570/262 |
| 810660 | 3/1981 | U.S.S.R. | 568/913 |

*Primary Examiner*—Wilbur Bascomb, Jr.

[57] ABSTRACT

Methylene chloride cannot be completely separated from methanol or ethanol by conventional distillation or rectification because of the mimimum boiling azeotrope. Methyelne chloride can be readily separated from methanol or ethanol by azeotropic or extractive distillation. Typical effective agents are: for methanol by azeotropic distillation, isopropanol or t-butanol; by extractive distillation, 1-nitropropane or n-butanol; for ethanol by extractive distillation, isobutanol or n-propyl acetate.

2 Claims, No Drawings

SEPARATION OF METHYLENE CHLORIDE FROM THE LOWER ALCOHOLS BY EXTRACTIVE DISTILLATION

FIELD OF THE INVENTION

This invention relates to a method for separating methylene chloride from methanol or ethanol using certain organic compounds as the agent in azeotropic or extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Methylene chloride, B.P.=40° C. forms a minimum boiling azeotrope with methanol, B.P.=64.6° C. at 38° C. containing 93% methylene chloride. Methylene chloride forms a minimum boiling azeotrope with ethanol, B.P.=78° C. at 39° C. containing 95% methylene chloride. The methylene chloride - alcohol azeotropes are impossible to separate by distillation because the relative volatility of an azeotrope is 1.0. Extractive distillation would be an attractive method of effecting the separation of methylene chloride from these alcohols if agents can be found that (1) will enhance the relative volatility between methylene chloride and these alcohols and (2) are easy to recover, that is, form no azeotrope with methylene chloride, methanol or ethanol and boil sufficiently above these three to make separation by rectification possible with only a few theoretical plates. Azeotropic distillation would also be an attractive method of separationg methylene chloride from the lower alcohols if agents can be found that will enhance the relative volatility sufficiently.

Extractive distillation typically requires the addition of an equal amount to twice as much extractive agent as the methylene chloride - alcohol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the methylene chloride and alcohols otherwise it will form a two phase azeotrope with it and some other method of separation will have to be employed.

| Relative Volatility | Theoretical Plates | Actual Plates. 75% Efficiency | Actual Plates. 75% Eff., Min.Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. When ordinary rectification is used, 87 actual plates of 75% efficiency are required at minimum reflux ratio to separate methylene chloride from alcohols in 99% purity. If extractive distillation is employed with an agent that converts the relative volatility to 1.7, only 29 actual plates are required.

OBJECTIVE OF THE INVENTION

The objects of this invention are to provide a process or method of azeotropic or extractive distillation that will enhance the relative volatility of methylene chloride to methanol or ethanol in their separation in a rectification column. It is a further object of this invention to identify organic compounds that are stable, can be separated from the methylene chloride or alcohols by rectification with relatively few plates and can be recycled to the extractive or azeotropic distillation column with little decomposition.

SUMMARY OF THE INVENTION

The objects of this invention are provided by a process for the separation of methylene chloride from methanol or ethanol which entails the use of certain organic compounds as the agent in azeotropic or extractive distillation.

DETAILED DESCRIPTION OF THE INVENTION

We have discovered that certain organic compounds will effectively increase the relative volatility between methylene chloride and methanol or ethanol and permit the separation of methylene chloride from methanol or ethanol by rectification when employed as the agent in azeotropic or extractive distillation. Table 2 lists the agents that we have found to be effective azeotrope formers to recover methylene chloride from methanol. The data in Tables 2, 3, 4, 6 and 7 was obtained in a vapor-liquid equilibrium still. In every case, the starting mixture was the methylene chloride- methanol or ethanol azeotrope. The relative volatilities are listed for each of the agents. The compounds which are effective azeotrope formers to remove methylene chloride from methanol are isopropanol, n-propanol, t-butanol, 2-butanol, methyl acetate, ethyl acetate, dioxane, vinyl n-butyl ether, vinyl isobutyl ether, 2-pentanone, diisobutyl ketone, n-propyl acetate, isobutyl acetate, isoamyl acetate, 3-pentanone, 3-hexanone, 2-hexanone, methyl isobutyl ketone, 2-heptanone, 4-methyl-2-pentanone, 3-heptanone, propylene glycol methyl ether, n-butyl acetate and triethyl amine. The starred compounds bring methanol out as overhead, the others bring out methylene chloride as overhead.

Table 3 lists the agents that we have found to be effective extractive distillation agents to recover methylene chloride from methanol. The compounds which are effective extractive distillation agents to remove methylene chloride from methanol are n-butanol, n-amyl acetate, propoxypropanol, butoxypropanol, ethanolamine, diethanolamine, acetonitrile, morpholine, ethylene glycol methyl ether, propylene glycol methyl ether, ethylene glycol butyl ether, ethylene glycol hexyl ether, mesityl oxide, acetic acid, nitromethane, nitroethane, 1-nitropropane and 2-nitropropane. The starred compounds bring methanol out as overhead, the others bring methylene chloride out as overhead.

Table 4 lists a number of compounds that proved to be ineffective as azeotropic or extractive distillation agents in the separation of methylene chloride from methanol.

Two of the agents whose relative volatility had been determined in the vapor-liquid equilibrium still were then evaluated in a glass perforated plate rectification column possessing 7.3 theoretical plates and the results listed in Table 5. 1-Nitropropane gave a relative volatility of 1.16 after two hours of operation. n-Butanol gave a relative volatility of 2.1 after two hours of continuous operation.

TABLE 2

Effective Azeotropic Agents For Separating Methylene Chloride From Methanol

| Compounds | Relative Volatility |
|---|---|
| n-Propanol | 2.1 |
| Methyl acetate | 1.4* |
| Ethyl acetate | 1.4* |
| Isopropanol | 2.8* |
| t-Butanol | 1.7 |
| Dioxane | 1.3* |
| Vinyl n-butyl ether | 1.5* |
| Vinyl isobutyl ether | 1.5* |
| 2-Pentanone | 1.4* |
| Diisobutyl ketone | 1.6* |
| n-Propyl acetate | 1.2* |
| Isobutyl acetate | 1.5* |
| Isoamyl acetate | 1.2* |
| 3-Pentanone | 2.2* |
| 3-Hexanone | 1.2 |
| 2-Hexanone | 1.2 |
| 2-Heptanone | 1.8* |
| 4-Methyl-2-pentanone | 1.7* |
| Methyl isobutyl ketone | 2.4* |
| 3-Heptanone | 1.6* |
| 2-Butanol | 3.9 |
| Propylene glycol methyl ether | 1.9 |
| n-Butyl acetate | 3.5* |
| Triethyl amine | 1.6 |

*Brings Methanol out as Overhead

TABLE 3

Effective Extractive Agents For Separating Methylene Chloride From Methanol

| Compounds | Relative Volatility |
|---|---|
| n-Butanol | 1.4* |
| n-Amyl acetate | 1.6* |
| Propoxypropanol | 2.1 |
| Butoxypropanol | 1.8 |
| Ethanolamine | 3.8 |
| Diethanolamine | 1.5* |
| Acetonitrile | 1.7* |
| Morpholine | 1.9 |
| Ethylene glycol methyl ether | 2.2 |
| Propylene glycol methyl ether | 1.5 |
| Ethylene glycol butyl ether | 2.3 |
| Ethylene glycol hexyl ether | 1.5 |
| Mesityl oxide | 1.5* |
| Acetic acid | 2.7 |
| Nitromethane | 1.3* |
| Nitroethane | 1.5* |
| 1-Nitropropane | 1.2* |
| 2-Nitropropane | 1.4* |

*Brings Methanol Out As Overhead

TABLE 4

Ineffective Agents For Separating Methylene Chloride From Methanol

| | |
|---|---|
| Methyl ethyl ketone | 3-Methyl-2-butanone |
| Methyl isoamyl ketone | 3-Octanone |
| N-Methyl morpholine | Ethylene glycol ethyl ether |
| N-Methyl ethanolamine | Propylene glycol isobutyl ether |
| Propionic acid | Ethylene glycol methyl ether acetate |
| Nitrobenzene | Propylene glycol dimethyl ether |
| 2-Methoxyethyl ether | |

TABLE 5

Data From Runs Made In Rectification Column-Methylene Chloride From Methanol

| Agent | Column | Time hrs. | Weight % $CH_2Cl_2$ | Weight % MeOH | Relative Volatility |
|---|---|---|---|---|---|
| 1-Nitropropane | Overhead | 1 | 13.1 | 86.9 | 1.157* |
| | Bottoms | | 30.2 | 69.2 | |
| 1-Nitropropane | Overhead | 2 | 15.7 | 84.3 | 1.16* |
| n-Butanol | Overhead | 1 | 99.7 | 0.3 | 1.8 |
| | Bottoms | | 81.8 | 18.2 | |
| n-Butanol | Overhead | 1.5 | 99.86 | 0.14 | 2.1 |
| | Bottoms | | 78.05 | 21.95 | |

*Brings Methahol Out As Overhead

Table 6 lists the agents that we have found to be effective extractive distillation agents to recover methylene chloride from ethanol. The compounds which are effective extractive distillation agents to remove methylene chloride from ethanol are nitromethane, 2-nitropropane, n-butanol, 2-butanol, n-propanol, 2-methyl butanol, t-butanol, 3-methyl-1-butanol, 2-methyl pentanol, t-amyl alcohol, n-hexanol, amyl acetate, 3-hexanone, 3-heptanone, methyl isobutyl ketone, 3,3-dimethyl-2-butanone, ethyl acetate, n-propyl acetate, n-butyl acetate, isobutyl acetate, ethylene glycol ethyl ether, ethylene glycol methyl ether, propylene glycol methyl ether, amyl formate and 2-methyl-1-butanol.

TABLE 6

Effective Extractive Agents For Separating Methylene Chloride From Ethanol

| Compounds | Relative Volatility |
|---|---|
| Nitromethane | 1.4 |
| 2-Nitropropane | 1.2 |

TABLE 6-continued

Effective Extractive Agents For Separating Methylene Chloride From Ethanol

| Compounds | Relative Volatility |
|---|---|
| n-Butanol | 2.1 |
| Amyl acetate | 1.9 |
| 3-Hexanone | 1.3 |
| 3-Heptanone | 1.4 |
| 2-Butanol | 2.0 |
| Methyl isobutyl ketone | 1.5 |
| n-Propanol | 2.0 |
| 2-Methyl butanol | 2.8 |
| t-Butanol | 1.5 |
| 3-Methyl-1-butanol | 3.0 |
| 2-Methyl pentanol | 3.1 |
| t-Amyl alcohol | 2.9 |
| n-Hexanol | 2.0 |
| 3,3-Dimethyl-2-butanone | 1.8 |
| Ethyl acetate | 1.5 |
| n-Propyl acetate | 1.9 |
| n-Butyl acetate | 1.6 |
| Isobutyl acetate | 1.5 |
| Ethylene glycol ethyl ether | 2.8 |
| Ethylene glycol methyl ether | 3.4 |
| Propylene glycol methyl ether | 2.1 |
| Amyl formate | 2.3 |

TABLE 7

Ineffective Agents For Separating Methylene Chloride From Ethanol

| | |
|---|---|
| Nitroethane | 1-Nitropropane |
| 2-Heptanone | 3-Methyl-2-butanone |
| Methyl acetate | |

TABLE 8

Data From Runs Made In Rectification Column-Methylene Chloride From Ethanol

| Agent | Column | Time hrs. | Weight % CH$_2$Cl$_2$ | Weight % Ethanol | Relative Volatility |
|---|---|---|---|---|---|
| Isobutanol | Overhead | 1 | 99.5 | 0.5 | 1.9 |
| | Bottoms | | 67.5 | 32.5 | |
| Isobutanol | Overhead | 2 | 99.1 | 0.9 | 1.75 |
| | Bottoms | | 63.9 | 36.1 | |
| n-Propyl Acetate | Overhead | 1 | 99.2 | 0.8 | 1.48 |
| | Bottoms | | 87.5 | 12.5 | |
| n-Propyl Acetate | Overhead | 2 | 98.2 | 1.8 | 1.28 |
| | Bottoms | | 90.2 | 9.8 | |

Table 7 lists a number of compounds that proved to be ineffective as azeotropic or extractive distillation agents in the separation of methylene chloride from ethanol.

Two of the agents whose relative volatility had been determined in the vapor-liquid equilibrium still were then evaluated in a glass perforated plate rectification column possessing 7.3 theoretical plates and the results listed in Table 8. Isobutanol gave a relative volatility of 1.9 after one hour of operation. n-Propyl acetate gave a relative volatility of 1.48 after one hour of operation.

THE USEFULNESS OF THE INVENTION

The usefulness or utility of this invention can be demonstrated by referring to the data presented in Tables 2 to 8. All of the successful agents show that methylene chloride can be separated from methanol or ethanol by means of azeotropic or extractive distillation in a rectification column and that the ease of separation as measured by relative volatility is considerable.

WORKING EXAMPLES

Example 1: Forty grams of the methylene chloride - methanol azeotrope and 30 grams of isopropanol as the azeotrope former were charged to a vapor-liquid equilibrium still and refluxed for two hours. Analysis indicated a vapor composition of 5.2% methanol, 13.3% methylene chloride and 81.5% isopropanol; a liquid composition of 6.8% methanol, 48.1% methylene chloride and 45.1% isopropanol which is a relative volatility of methanol to methylene chloride of 2.8.

Example 2: Forty grams of the methylene chloride - methanol azeotrope and 30 grams of t-butanol as the azeotrope former were charged to the vapor-liquid equilibrium still and refluxed for two hours. Analysis indicated a vapor composition of 93.7% methylene chloride, 6.3% methanol; a liquid composition of 89.6% methylene chloride, 10.4% methanol which is a relative volatility of methylene chloride to methanol of 1.5.

Example 3: Fifty grams of the methylene chloride - methanol azeotrope and 30 grams of nitroethane were charged to the vapor-liquid equilibrium still and refluxed for three hours. Analysis indicated a vapor composition of 13% methanol, 87% methylene chloride; a liquid composition of 9.1% methanol, 90.9% methylene chloride which is a relative volatility of methanol to methylene chloride of 1.5.

Example 4: Fifty grams of the methylene chloride - methanol azeotrope and 30 grams of propylene glycol methyl ether were charged to the vapor-liquid equilibrium still and refluxed for three hours. Analysis indicated a vapor composition of 89.7% methylene chloride, 10.3% methanol; a liquid composition of 85.4% methylene chloride, 14.6% methanol which is a relative volatility of methylene chloride to methanol of 1.5.

Example 5: A solution comprising 186 grams of methylene chloride and 14 grams of methanol was placed in the stillpot of a 7.3 theoretical plate rectification column. When refluxing began, an extractive agent comprising n-butanol was pumped into the column at a rate of 15 ml/min. The temperature of the extractive agent as it entered the column was 85° C. After establishing the feed rate of the extractive agent, the heat input to the methylene chloride - methanol in the stillpot was adjusted to give a total reflux rate of 40 ml/min. After 1.5 hours of operation, the overhead and bottoms samples of approximately two ml. were collected and analysed. The overhead analysis was 99.86% methylene chloride, 0.14% methanol and the bottoms analysis was 78.05% methylene chloride, 21.95% methanol. This gives an average relative volatility of 2.1 for each theoretical plate. This data is presented in Table 5.

Example 6: Eighty grams of the methylene chloride - ethanol azeotrope and 30 grams of n-propyl acetate were charged to the vapor-liquid equilibrium still and refluxed for three hours. Analysis indicated a vapor composition of 96% methylene chloride, 4% ethanol; a liquid composition of 92.7% methylene chloride, 7.3% ethanol which is a relative volatility of methylene chloride to ethanol of 1.9.

Example 7: Fifty grams of the methylene chloride - ethanol azeotrope and 30 grams of 2-methyl butanol were charged to the vapor-liquid equilibrium still and refluxed for six hours. Analysis indicated a vapor composition of 96.3% ethanol, 3.7% methylene chloride; a liquid composition of 90% ethanol, 10% methylene chloride which is a relative volatility of ethanol to methylene chloride of 2.8.

Example 8: A solution comprising 190 grams of methylene chloride and 20 grams of ethanol was placed in the stillpot of the 7.3 theoretical plate rectification column. When refluxing began, an extractive agent comprising isobutanol was pumped into the column at a rate of 15 ml/min. The temperature of the extractive agent as it entered the column was 85° C. After establishing the feed rate of the extractive agent, the heat input to the methylene chloride - ethanol in the stillpot was adjusted to give a total reflux rate of 40 ml/min. After one hour of operation, the overhead and bottoms samples of approximately two ml. were collected and analysed. The overhead analysis was 99.5% methylene chloride, 0.5% ethanol and the bottoms analysis was 67.5% methylene chloride, 32.5% ethanol. This gives an average relative volatility of 1.9 for each theoretical plate. This data is presented in Table 8.

We claim:

1. A method for recovering methanol from a mixture of methanol and methylene chloride which comprises distilling a mixture of methanol and methylene chloride in the presence of about one part of an extractive agent per part of methanol - methylene chloride mixture, recovering the methanol as overhead product and obtaining the methylene chloride and the extractive agent from the stillpot, wherein said extractive agent consists of one material selected from the group consisting of n-butanol, n-amyl acetate, diethanolamine, acetonitrile, mesityl oxide, nitromethane, nitroethane, 1-nitropropane and 2-nitropropane.

2. A method for recovering methylene chloride from a mixture of methylene chloride and ethanol which comprises distilling a mixture of methylene chloride and ethanol in the presence of about one part of an extractive agent per part of methylene chloride - ethanol mixture, recovering the methylene chloride as overhead product and obtaining the ethanol and the extractive agent from the stillpot, wherein said extractive agent consists of one material selected from the group consisting of nitromethane, 2-nitropropane, n-butanol, amyl acetate, 3-hexanone, 3-heptanone, 2-butanol, methyl isobutyl ketone, n-propanol, t-butanol, 2-methyl-1-butanol, 3-methyl-1-butanol, 2-methyl pentanol, t-amyl alcohol, n-hexanol, 3,3-dimethyl-2-butanone, ethyl acetate, n-propyl acetate, n-butyl acetate, isobutyl acetate, ethylene glycol ethyl ether, ethylene glycol methyl ether, propylene glycol methyl ether and amyl formate.

* * * * *